US007727192B2

(12) United States Patent
Tokumoto et al.

(10) Patent No.: US 7,727,192 B2
(45) Date of Patent: Jun. 1, 2010

(54) PUNCTURE ADAPTER FOR USE IN ULTRASONIC DIAGNOSIS

(75) Inventors: Tadahiko Tokumoto, Tokyo (JP); Wataru Takekawa, Mitaka (JP); Tomohiro Kurimoto, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 1080 days.

(21) Appl. No.: 11/176,074

(22) Filed: Jul. 7, 2005

(65) Prior Publication Data
US 2006/0020211 A1    Jan. 26, 2006

(30) Foreign Application Priority Data

| Jul. 9, 2004 | (JP) | ............................. 2004-202923 |
| May 30, 2005 | (JP) | ............................. 2005-156728 |

(51) Int. Cl.
*A61M 5/00*      (2006.01)
*A61B 8/14*      (2006.01)

(52) U.S. Cl. ........................................ 604/116; 600/464
(58) Field of Classification Search ................. 600/437, 600/461, 464; 604/116; 606/108
See application file for complete search history.

(56) References Cited

U.S. PATENT DOCUMENTS

| 5,052,396 | A | * | 10/1991 | Wedel et al. ................. 600/461 |
| 5,381,794 | A | * | 1/1995 | Tei et al. ..................... 600/459 |
| 5,941,889 | A | * | 8/1999 | Cermak ....................... 606/130 |
| 5,993,463 | A | * | 11/1999 | Truwit ........................ 606/130 |
| 6,361,499 | B1 | * | 3/2002 | Bates et al. .................. 600/461 |
| 6,379,307 | B1 | * | 4/2002 | Filly et al. ................... 600/461 |

FOREIGN PATENT DOCUMENTS

| JP | 58-33010 | 3/1983 |
| JP | 60-92747 | 5/1985 |
| JP | 04-303440 | 10/1992 |
| JP | 11-33026 | 2/1999 |
| JP | 11-347037 | 12/1999 |
| JP | 2001-120553 | 5/2001 |
| JP | 2002-301074 | 10/2002 |
| JP | 2003-000593 | 1/2003 |
| JP | 2004-49320 | 2/2004 |
| JP | 2005-204696 | 8/2005 |

* cited by examiner

*Primary Examiner*—Nicholas D Lucchesi
*Assistant Examiner*—Rebecca E Eisenberg
(74) *Attorney, Agent, or Firm*—William L. Androlia; H. Henry Koda

(57) ABSTRACT

An adapter for use in puncture (a puncture adapter) for performing puncture while an ultrasonic image is being observed. The puncture adapter is composed of a holder for holding a probe which transmits and receives an ultrasonic wave, and a base unit for movably supporting the holder. A guide mechanism provided in the base unit guides a puncture needle. Moving the probe held in the holder moves a beam scan plane, and the intersection between the beam scan plane and a puncture route can be moved along the puncture route. The base unit functions as a seat which is brought into contact with a surface of a living body. A plurality of projecting legs may be provided on the base unit. The plurality of projecting legs are provided along the periphery of the movement region in which the wave transmitting and receiving surface of the probe moves.

15 Claims, 15 Drawing Sheets

PUNCTURE ADAPTER FOR USE IN ULTRASONIC DIAGNOSIS

BACKGROUND OF THE INVENTION

1. Field of the Invention

The present invention relates to an adapter for use in puncture (or centesis), and more particularly to an adapter which is attached to a probe and guides a puncture needle.

2. Description of Related Art

An adapter for use in puncture (which will be hereinafter referred to as a "puncture adapter") is used for performing puncture with respect to a target tissue through a surface of a living body while an ultrasonic image of the target tissue within the living body is observed. Generally, such an adapter is detachably mounted onto a probe and holds and guides a puncture needle. Japanese Patent Laid-Open Publications Nos. Sho 60-92747, Hei 4-303440, and 2001-120553 describe a puncture adapter which guides a puncture needle such that a puncture route of the puncture needle coincides with (or is included in) a scan plane which is formed by scanning of an ultrasonic beam. More specifically, a guide unit for the puncture needle is provided above one end side of the scan plane and the puncture needle is guided therefrom in the diagonal direction so as to advance on the scan plane. This guiding structure allows an operator to observe, on a tomographic image corresponding to the scan plane, how the puncture needle is gradually introduced, thereby assisting the operator to perform puncture with respect to the target tissue at the optimal angle or in the optimal direction.

With the conventional puncture system described above, while it is possible to observe the structure of a tissue located on the scan plane including the puncture route, the tissue before and behind the scan plane cannot be observed. For example, the carotid artery and jugular vein run adjacent to each other in the neck portion of a human body. When one wishes to insert a puncture needle into the jugular vein in the diagonal direction with respect to the axial direction of the jugular vein in order to insert a catheter, it is desired that the puncture is performed while both the carotid artery and the adjacent jugular vein are being observed simultaneously on a tomographic image. To do so, it may be possible to fix the guide unit for the puncture needle above the region anterior or posterior of the scan plane and guide the puncture needle therefrom in the diagonal direction, i.e. in the direction in which the puncture needle penetrates the scan plane diagonally. However, while such a structure allows observation of a transverse section of each blood vessel on the tomographic image, this structure has a disadvantage that the position of the tip of the puncture needle cannot be recognized on the image until the tip reaches the scan plane. In other words, it is not possible to confirm the route through which the puncture needle is being introduced within the living body on the tomographic image. This problem similarly exists in cases where puncture is performed with respect to portions other than the neck.

SUMMARY OF THE INVENTION

One advantage of the present invention is that it enables an operator to confirm a puncture needle positioned at various insertion depths on an ultrasonic image in a case wherein a puncture route is set in a direction in which the puncture needle penetrates through the scanning plane.

Another advantage of the present invention is that it allows observation of a whole three-dimensional space including the puncture route of the puncture needle using a tomographic image.

(1) According to one aspect of the present invention, an adapter for use in puncture to be attached to a probe which transmits and receives an ultrasonic wave comprises a holder for holding the probe; and a base unit including a guide mechanism for guiding a puncture needle and a moving mechanism for movably supporting the holder to move a wave transmitting and receiving region of the ultrasonic wave relative to a puncture route of the puncture needle.

With the above structure, the probe is held by the holder, which is then movably supported by the moving mechanism of the base unit. The guide mechanism provided in the base unit guides a puncture needle into a body at a predetermined angle (or at a selected angle). In the process of inserting the puncture needle into the body, by moving the probe along with the holder, the wave transmitting and receiving region generated by the probe also moves within the living body, so that the puncture needle (particularly the tip thereof) located at various depths can be observed on an ultrasonic image. For example, even when the wave transmitting and receiving region is a two-dimensional scan plane (a beam scan plane), movement of such a scan plane forward and backward will resultantly allow observation of a whole three-dimensional space as a tomograhic image which changes dynamically.

The probe may be a convex type probe having a wave transmitting and receiving surface in the shape of a convex surface or a linear type probe having a wave transmitting and receiving surface in the shape of a flat surface. Of course, other types of probes may also be used. The holder and the probe are basically formed as separate members. The holder, however, can be formed integrally with the probe. More specifically, a mechanism for coupling the probe to the base unit may be provided in the probe itself. Preferably, the guide mechanism guides the puncture needle along the puncture route which is inclined at a predetermined angle with respect to the base unit. A mechanism for changing the puncture angle continuously or stepwise may be provided. Preferably, the wave transmitting and receiving region corresponds to a two-dimensional beam scan plane, and has a rectangular or sector shape. The mechanism according to the present invention may also be adopted when the wave transmitting and receiving region is a three-dimensional region.

Preferably, the moving mechanism causes the holder to rotate, i.e. pivot, about a predetermined horizontal axis of rotation. In this case, it is desirable to position the axis of rotation such that the wave transmitting and receiving surface of the probe is continuously in close contact with the surface of the living body. The position at which the probe is held may be fixed or varied in the holder. Further, it is also possible to prepare a plurality of types of holders and select a holder in accordance with the type of the probe to be used. This structure is advantageous in that a base unit can be shared by various types of probes. The moving mechanism may include, in addition to the type described above, a mechanism for causing the probe to translate (slide), a mechanism for causing the probe to rotate using the vertical center axis of the probe as the axis of rotation, and so on. In any case, by configuring the moving mechanism such that the wave transmitting and receiving region can be moved relative to the puncture route, an image over a wide space can be observed.

While the moving mechanism described above is driven by a user, the moving mechanism may be configured to be driven automatically. Further, a sensor for detecting the moving position of the holder, namely the moving position of the probe, may be provided.

Preferably, the moving mechanism moves the holder such that a beam scan plane which is the wave transmitting and receiving region intersects the puncture route and an intersection between the puncture route and the beam scan plane moves along the puncture route.

With the moving mechanism as described above, the probe is moved so that a cross section of the puncture needle (in particular a cross section of the tip of the puncture needle) can be confirmed on a tomographic image. When confirming the position of the tip end of the puncture needle, the probe is first moved quickly in a large motion for specifying the puncture needle on the tomographic image, and, once the puncture needle is specified, slow and small reciprocating movement of the probe are then repeated so as to detect the tip end of the puncture needle. When the tip of the puncture needle is specified, the tip of the puncture needle and the structure of the tissue within the body appear on the tomographic image, whereby it is possible to confirm whether or not the puncture needle advances toward the target tissue in a correct manner. In other words, security of the puncture can be enhanced. Further, various types of usage of the adapter of the present invention other than the usage described above may also be considered.

Preferably, the moving mechanism causes the holder to pivot about a rotation center axis (axis of rotation) which is spaced apart from the puncture route. The rotation center axis is preferably set in the horizontal direction at a position which is spaced apart from the subject, i.e. the surface of the living body, by a predetermined offset distance. The rotation center axis may be set on the surface of the living body, or the position of the rotation center axis may be varied in accordance with the type of probe, for example.

Preferably, the moving mechanism restricts pivoting movement of the holder such that the intersection moves in a range from a first observation position at a shallower depth on the puncture route to a second observation position at a deeper depth on the puncture route. With this structure, the movement range of the probe can be restricted within a necessary range. Such a movement range may be variably set. When the inclination angle of the puncture needle is variable, the movement range may be variably set in accordance with the inclination angle.

Preferably, the holder is a member which detachably holds the probe while directing a wave transmitting and receiving surface of the probe toward a subject, and the holder is removably assembled onto the base unit. It is desirable that each member can be separated from each other for the purpose of cleaning, disinfection, sterilization or the like. Further, it is desirable to form the puncture adapter by a material which can resist high-pressure sterilization using an autoclave.

Preferably, the guide mechanism is a mechanism for holding and releasing the puncture needle and guides the puncture needle in the direction which is inclined with respect to the base unit. With the above structure in which the puncture needle can be released after completion of puncture, the probe and the adapter can also be detached from the puncture needle easily. This structure also facilitates the subsequent operations including insertion of a catheter, injection of a medicine, or the like.

Preferably, the guide mechanism includes a lever which opens and closes a guide hole through which the puncture needle is inserted, and the guide hole is opened and closed by a sliding operation of the lever. It is desirable to configure the guide mechanism such that the lever can be operated by one hand which holds the probe.

Preferably, the guide mechanism includes a fixed piece and a sliding piece which performs sliding movement with respect to the fixed piece for holding and releasing the puncture needle, a recess is formed on one of the fixed piece and the sliding piece, and a projection which is fitted down into the recess when the sliding piece advances and which is withdrawn from the recess when the sliding piece retreats is formed on the other one of the fixed piece and the sliding piece.

With the above structure, when the sliding piece advances, the projection is fitted in the recess, whereby the position of the sliding piece is stably held. Specifically, it is possible to prevent the sliding piece from retreating inadvertently to thereby release the holding state of the puncture needle. By causing the sliding piece to retreat in response to force applied by a user, the projection is withdrawn from the recess, thereby forcibly releasing the holding state of the puncture needle. It is desirable to provide the projection on the leading end of the elastic piece.

Preferably, the base unit includes a seat which is brought in contact with a surface of the subject, the seat having a pair of leg portions provided with a movement region of the wave transmitting and receiving surface of the probe interposed therebetween. By bringing the adapter in contact with the surface of the living body by a relatively large area so as to avoid the region above the target tissue, a pressing force generated at the time of such contact is dispersed, whereby the problem that the target tissue within the living body is collapsed or deformed more than necessary can be prevented.

Preferably, each of the leg portions has a flat contact surface extending in parallel to each other in the moving direction of the wave transmitting and receiving surface. With this structure, when the target of puncture is a blood vessel, it is possible to bring the base unit in contact with the surface of the subject in the region located on both sides of the blood vessel while avoiding the region immediately above the blood vessel. The shape of the contact surface may be a rectangle or a shape formed by removing one of four sides of a rectangle.

(2) In accordance with another aspect of the present invention, an adapter for use in puncture to be attached to a probe which transmits and receives an ultrasonic wave for performing puncture with respect to a target blood vessel under observation on a tomographic image comprises a holder for holding the probe; and a base unit to be disposed on a surface of a subject, the base unit movably supporting the holder, wherein the base unit includes a seat which is brought in contact with the surface of the subject; a guide mechanism for guiding a puncture needle with respect to the target blood vessel in a diagonal direction along the axial direction of the target blood vessel; and a moving mechanism for movably supporting the holder which holds the probe, such that a beam scan plane generated by the probe intersects a puncture route of the puncture needle and the target blood vessel in each movement position.

Here, the diagonal direction along the axial direction of the target blood vessel refers to a direction which, when a vertical plane including the center axis of the target blood vessel (corresponding to the plane shown in FIG. 8, which will be described below, for example) is defined, exists on the vertical plane and diagonally intersects the center axis of the target blood vessel.

Preferably, the moving mechanism is a mechanism for causing the holder to perform pivoting movement, the puncture route is fixed independent of the pivoting movement of the holder, and an intersection between the beam scan plane and the puncture route moves along a center line of the beam scan plane within a predetermined depth range. Preferably, the seat is brought in contact with a neck portion of the subject, and the target blood vessel is a jugular vein.

With the above structure, the adapter is positioned on the body surface using the target blood vessel (a jugular vein, for example) as a reference, and the adapter can be used for performing puncture and ultrasonic diagnosis without applying an unnecessary pressing force onto the target blood vessel. In particular, because puncture can be performed while observing a tomographic image of the cross section which intersects the puncture route, puncture can be performed while safely confirming that blood vessels other than the target blood vessel are located outside the puncture route, or the like. Further, it is desirable that either one or both of the holder and the base unit are replaceable.

(3) In accordance with still another aspect of the present invention, an adapter for use in puncture to be attached to a probe which transmits and receives an ultrasonic wave comprises a holder for holding the probe; and a base unit including a guide mechanism for guiding a puncture needle and a moving mechanism for movably supporting the holder to move a wave transmitting and receiving region of the ultrasonic wave relative to a puncture route of the puncture needle, wherein the base unit includes a plurality of projecting legs which are rounded and project, the plurality of projecting legs being provided along the periphery of a movement region of a wave transmitting and receiving surface of the probe and being brought in contact with a surface of a subject.

With the above structure, when the base unit is brought in contact with the surface of the subject, a pressing force concentrates on a plurality of projecting legs and the surface of the subject is depressed by each projecting leg. At the same time, a portion of the surface of the subject between pairs of the plurality of projecting legs is relatively lifted upwards, thereby coming in close contact with the wave transmitting and receiving surface of the probe. Thus, as a great pressing force is not applied from the wave transmitting and receiving surface of the probe onto the subject, it is possible to solve or reduce the problem that the target tissue, such as a blood vessel, existing immediately below the wave transmitting and receiving surface is collapsed by the pressing force. A plurality of projecting legs are provided at positions across the target tissue. While the number of the projecting legs is desirably four, three or five or more projecting legs may be configured. However, if a great number of projecting legs are formed close together, these projecting legs will provide an effect similar to that achieved by a pressing force generated by a plane, generally increasing the likelihood that the target tissue will be deformed or collapsed. It is therefore desirable to determine the number or arrangement of a plurality of projecting legs so as not to cause the above problems. When the tip end surface (contact surface) of each projecting leg is rounded, it is possible to prevent the living body from feeling pain or feeling uncomfortable.

Preferably, the plurality of projecting legs are provided at four positions corresponding to four corners of the movement region. Preferably, the plurality of projecting legs include a first projecting leg and a second projecting leg provided on one side of the movement region and a third projecting leg and a fourth projecting leg provided on the other side of the movement region, a first arch portion is formed between the first projecting leg and the second projecting leg, a second arch portion is formed between the third projecting leg and the fourth projecting leg, a third arch portion is formed between the first projecting leg and the third projecting leg, and a fourth arch portion is formed between the second projecting leg and the fourth projecting leg. Preferably, in a state wherein the base unit is pressed onto the surface of the subject, a pressing force is conveyed from the plurality of projecting legs to the subject, and consequently a portion of the surface of the subject within the movement region is relatively lifted upwards, and in the state wherein the portion of the surface of the subject is lifted upwards, the wave transmitting and receiving surface of the probe comes in contact with the portion of the surface of the subject independent of a moving position of the probe.

In the above structure, it is desirable that the tip end surface of each projecting leg is set at a position lower (or closer to the living body) than a position of the wave transmitting and receiving surface of the probe. Further, is it desirable that the ceiling surface of each arch portion is set at a position higher (or further from the living body) than a position of the wave transmitting and receiving surface of the probe.

As described above, according to the above structure, it is possible to set the puncture route in a direction which diagonally intersects (penetrates) the scan plane, and to observe the puncture needle located at various insertion depths on an ultrasonic image. Further, according to the present invention, it is possible to observe a tomographic image over a wide range of positions within a living body.

BRIEF DESCRIPTION OF THE DRAWINGS

Preferred embodiments of the present invention will be described in detail based on the following figures, wherein.

DETAILED DESCRIPTION OF PREFERRED EMBODIMENTS

Preferred embodiments of the present invention will be described in detail with reference to the accompanying drawings.

Figure 1:
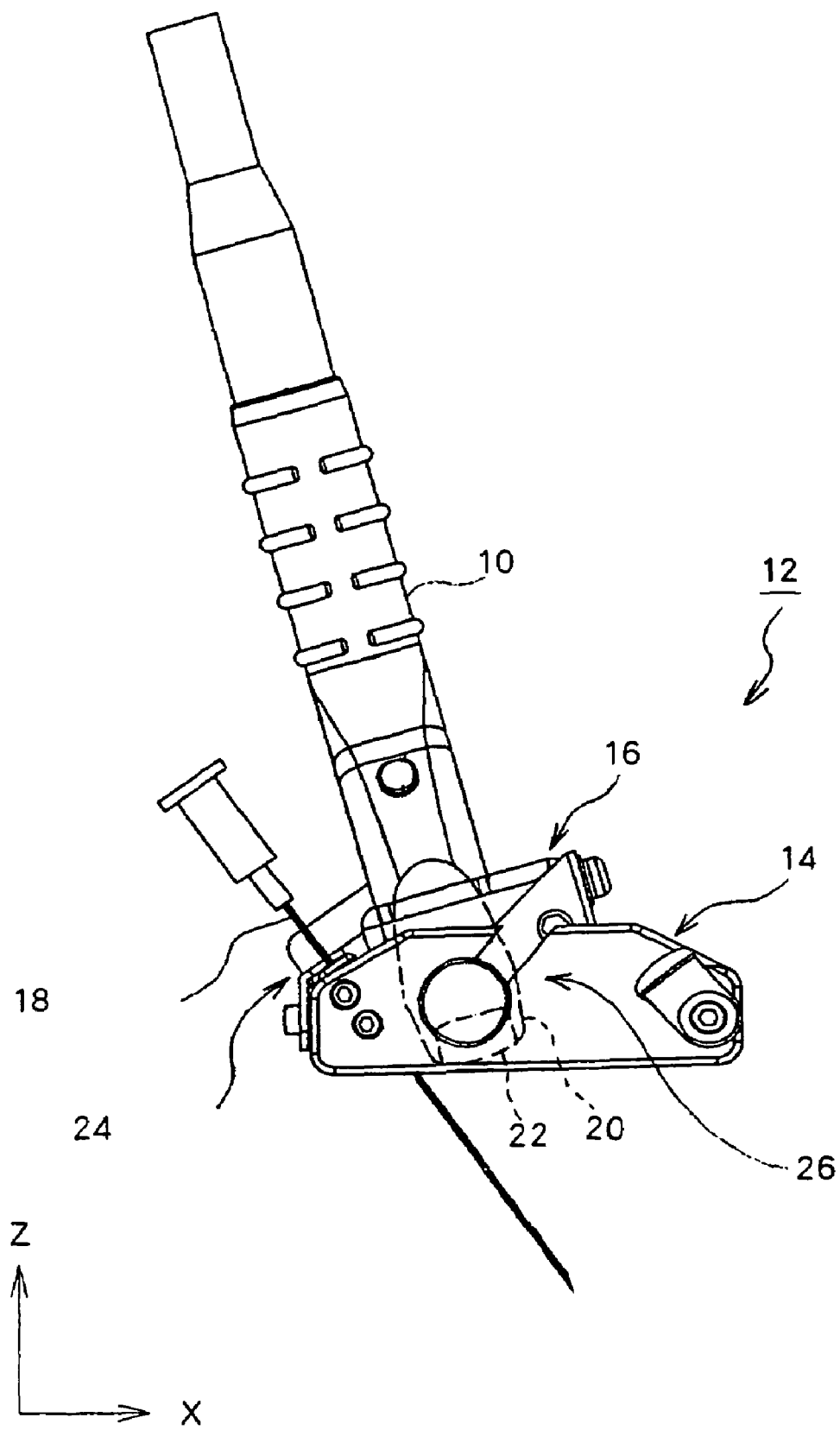
FIG. 1 is side view of an adapter for used in puncture according to one embodiment of the present invention.
Figure 2:
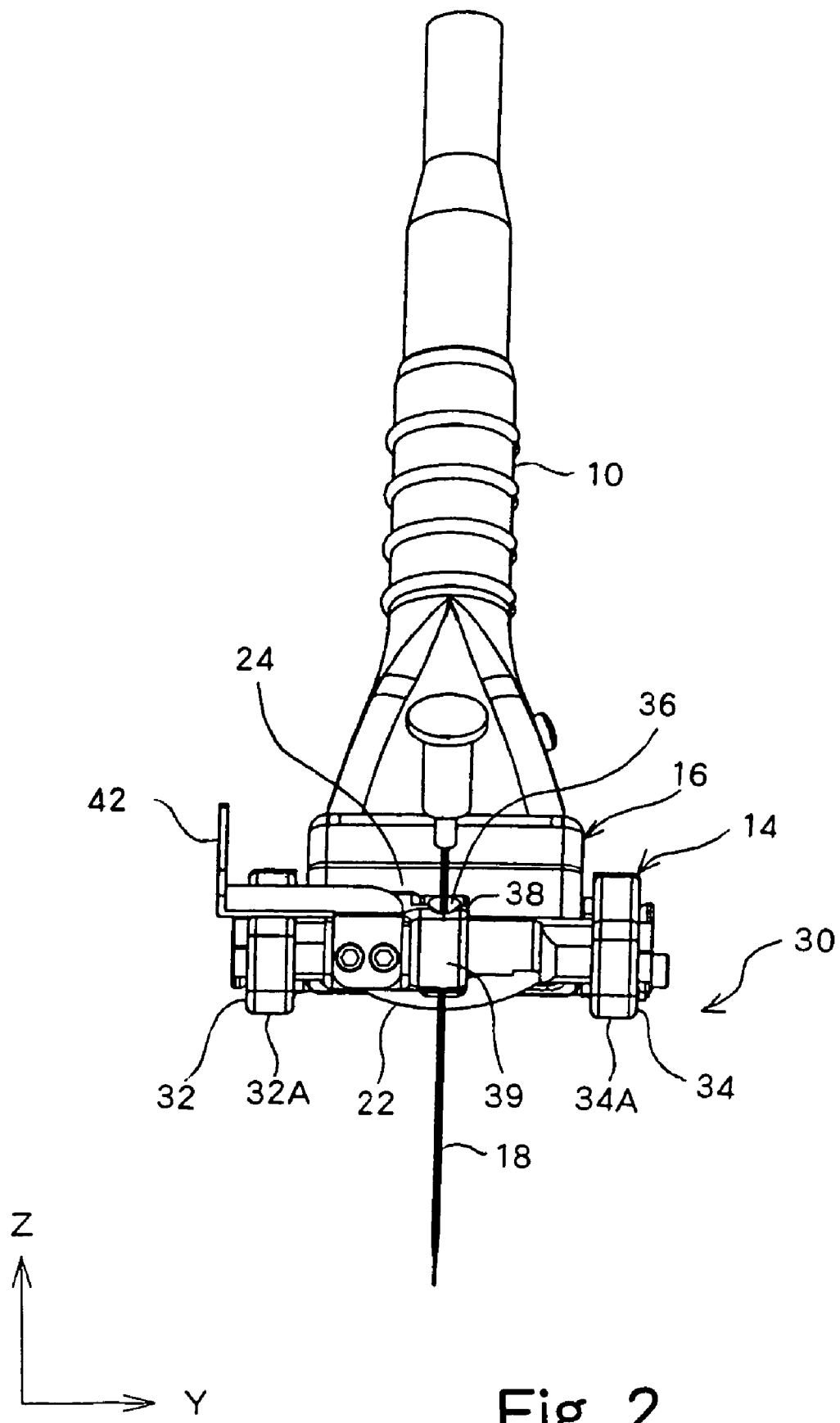
FIG. 2 is a front view of the puncture adapter according to the embodiment of the present invention.

FIG. 1 is a side view of an adapter for use in puncture (a puncture adapter) according to one embodiment of the present invention, and FIG. 2 is a front view of the puncture adapter.

Referring to FIG. 1, a puncture adapter 12 is used in direct contact with a surface of a subject, and is detachably mounted with respect to a probe 10. The puncture adapter includes a base unit 14 and a holder 16. The base unit 14 includes a guide mechanism 24 and a moving mechanism (supporting mechanism) 26, as will be described below. The guide mechanism 24 guides a puncture needle 18 at a predetermined inclined angle.

The holder 16 is a component which holds the probe 10. As shown in FIGS. 1 and 2, the tip portion 20 of the probe 10 is held by the holder 16. Within the tip portion 20 of the probe 10, a 1D array transducer (not shown) formed by a plurality of transducer elements arranged in an arc shape is provided in this embodiment. With electronic linear scanning of an ultrasonic beam generated by the array transducer, a sector-shape scan plane (beam scan plane) is formed, in other words, so-called convex scanning is performed. Here, the puncture adapter according to the present invention may be similarly used in cases where other type of probes are used. The probe 10 is connected, via a probe cable, to an ultrasonic diagnosis apparatus (not shown) which forms an ultrasonic image.

A wave transmitting and receiving surface of the probe 10, which is brought into contact with a body surface, is formed of an acoustic lens or the like. The moving mechanism 26 allows the holder 16 to rotate about a predetermined horizontal axis of rotation. With the rotation of the holder 16, the probe 10 which is held by the holder 16 also rotates or pivots, which further causes the scan plane generated by the probe 10 to also pivot. It is therefore possible to set the rotation angle of the holder 16 at a desired position, thereby allowing the setting of the scan plane at a desired position (at a desired inclined angle) within the subject. Further, by shifting the scan plane forward and backward, it is possible to search for a structure within the living body or the tip end of the puncture needle.

The puncture adapter 12 according to the present embodiment is especially suitable for performing puncture with respect to a jugular vein. When performing such puncture, the puncture adapter 12 is first brought into contact with a surface of the neck portion of a subject, and then the puncture needle 18 which is guided by the guide mechanism 24 is inserted diagonally along the axis direction of jugular vein into the jugular vein (see FIG. 8, which will be described below). By causing the probe 10 to pivot during this puncture process, the structure of the living body, particularly the tip end position of the puncture needle, can be observed, on a tomographic image, over the area covering the anterior and posterior regions of the scan plane.

FIG. 2 shows the guide structure 24 in detail. The guide mechanism 24 includes one piece 38 which functions as a fixed piece and the other piece 39 which functions as a slider. The other piece 39 can slidably move with respect to the one piece 38. A lever 42 is coupled with the other piece 39, and the one piece 38 and the other piece 39 can change their relative positions by the slide movement of the lever 42 in the Y direction in FIG. 2. When the lever 42 reaches the forward end in the Y direction, a guide hole 36 is formed, which serves as a passage through which the puncture needle is guided. More specifically, one recess formed on the one piece 38 and the other recess formed on the other piece 39 form the guide hole 36 when these recesses are aligned with each other. As shown in FIG. 2, the base unit 14 includes a seat 30 which further includes a pair of leg portions 32, 34 provided on both ends of the seat 30 with the wave transmitting and receiving region interposed therebetween in the Y direction.

The lower surfaces of the respective leg portions 32 and 34 form contact surfaces 32A and 34A, respectively, which extend in the X direction and are brought in contact with the surface of a living body. As not only the wave transmitting and receiving surface 22 of the probe 10 but also these contact surfaces 32A and 34A contact with the surface of the living body, a pressing force applied to the living body is dispersed, whereby a problem of deformation of an organ which is a subject of puncture within the living body, for example, can be prevented. Thus, such a structure can provide an advantage that the state of the structure within the living body can be maintained by the dispersed pressing force. Here, the wave transmitting and receiving surface 22 of the probe must be in closest contact with the surface of a living body, and this close contact must be maintained even when the probe 10 moves. It is therefore desirable to appropriately set an amount of downward projection of the pair of leg portions 32 and 34 in consideration of the relationship with respect to the shape and the height of the wave transmitting and receiving surface 22. Alternatively, it is desirable to configure the structure such that the amount of downward projection of the probe 10 can be set appropriately to a desired value in consideration of the amount of projection of the pair of legs 32 and 34. During the ultrasonic diagnosis, the entire probe 10 may be covered with a sterilization cover (not shown). Further, an acoustic propagation medium such as jelly is applied to the wave transmitting and receiving surface 22 in order to achieve preferable acoustic coupling between the wave transmitting and receiving surface and the surface of the living body.

The lever 42, which is provided near the tip portion of the probe 10 as shown in FIG. 2, can be operated using the hand holding the probe 10. More specifically, in a state where the probe 10 is held by the thumb and the forefinger, the lever 42 can be operated using the middle finger or the ring finger, which are not then being used. This structure makes it possible to hold the probe and operate the lever with one hand, freeing the other hand to operate the puncture needle 18.

Figure 3:
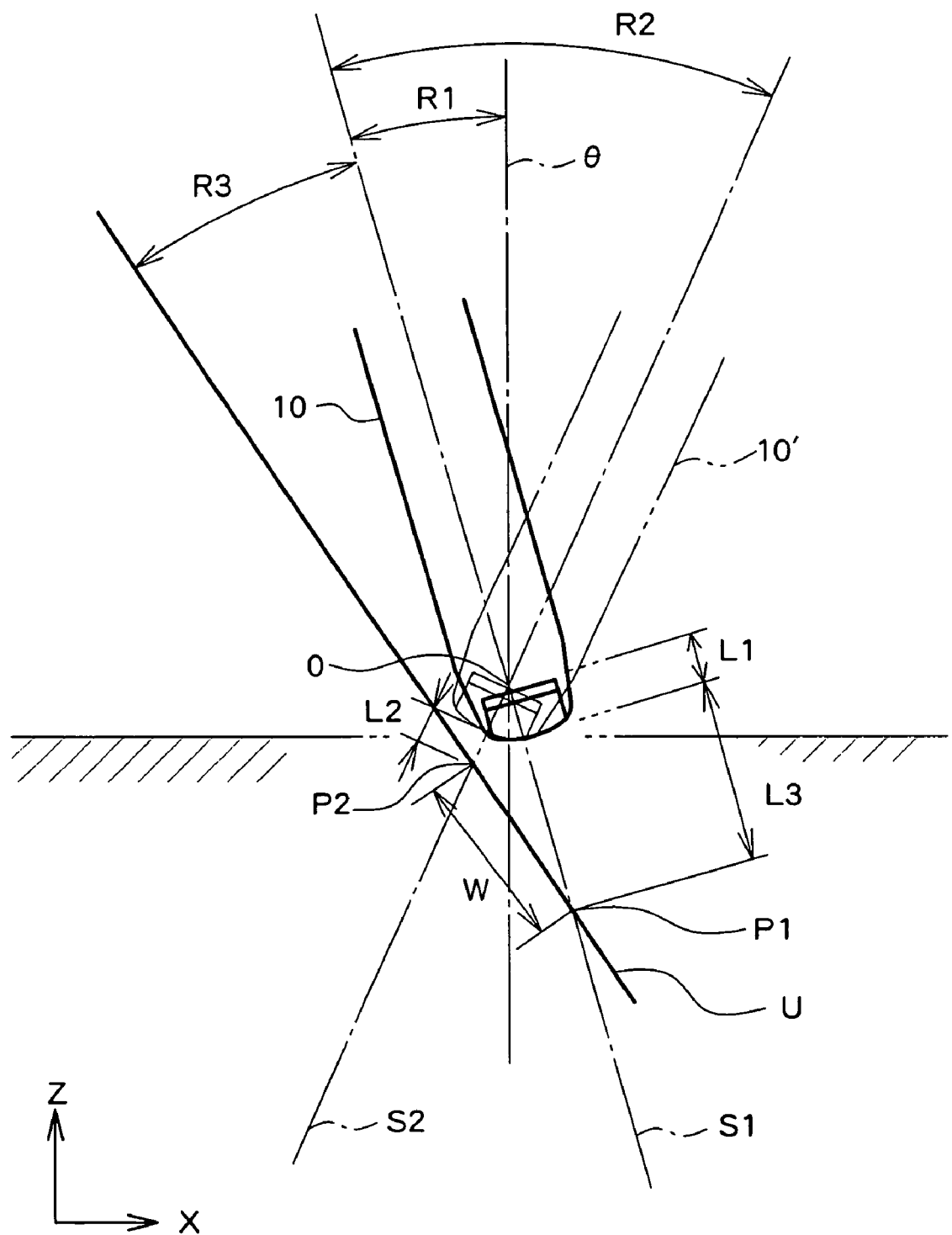
FIG. 3 is an explanatory view for explaining a relationship between a pivoting movement of the scan plane and the puncture route.

FIG. 3 shows a relationship between the puncture route and the scan plane. The probe 10 can perform pivoting movement in the right and left directions with respect to the vertical axis Q, as shown in FIG. 3. Referring to FIG. 3, the scan plane generated when the probe 10 is inclined by the greatest amount toward one side is represented as S1 and the scan plane generated when the probe 10 is inclined by the greatest amount toward the other side is represented as S2. As such, the probe 10 can perform pivoting movement over the angle range R2. Here, the R1 indicates an inclined angle of the probe 10 which is positioned at one inclination end. Then, the angle of the puncture route U is set so as to form the angle R3 with respect to the angle R1. The puncture route U is continuously fixed independent of the movement of the probe 10. For example, the angle R1 is 15 degrees, the angle R2 is 40 degrees, and the angle R3 is 30 degrees. In such a numerical relationship, the puncture route U is set at 45 degrees with respect to the surface of a living body, for example.

Referring further to FIG. 3, L1 denotes a distance between the apex of the wave transmitting and receiving surface and the rotation center axis O. Further, an intersection between the scan plane S1 at the one inclination end of the probe 10 and the puncture route U is represented as P1, and an intersection between the scan plane S2 at the other inclination end of the probe 10 and the puncture route U is represented as P2. The intersection P1 exists at a depth corresponding to the distance L3 from the wave transmitting and receiving surface to the intersection P1, and the intersection P2 exists at a depth corresponding to the distance L2 from the wave transmitting and receiving surface to the intersection P2. As will be understood from the above relationship, by causing the probe 10 to pivot, i.e. by causing the scan plane to pivot, the above-described intersection moves on the puncture route U over the range W. Specifically, while in the conventional art tissue in front of or in back of the scan plane cannot be observed on a tomographic image, according to the present embodiment, observation on the image can be performed over the whole three dimensional space by shifting the scan plane itself forward and backward. In other words, it is possible to easily specify, on an image, the position of the tip of the puncture needle located at various insertion depths, along the puncture route which intersects the scan plane.

Figure 4:
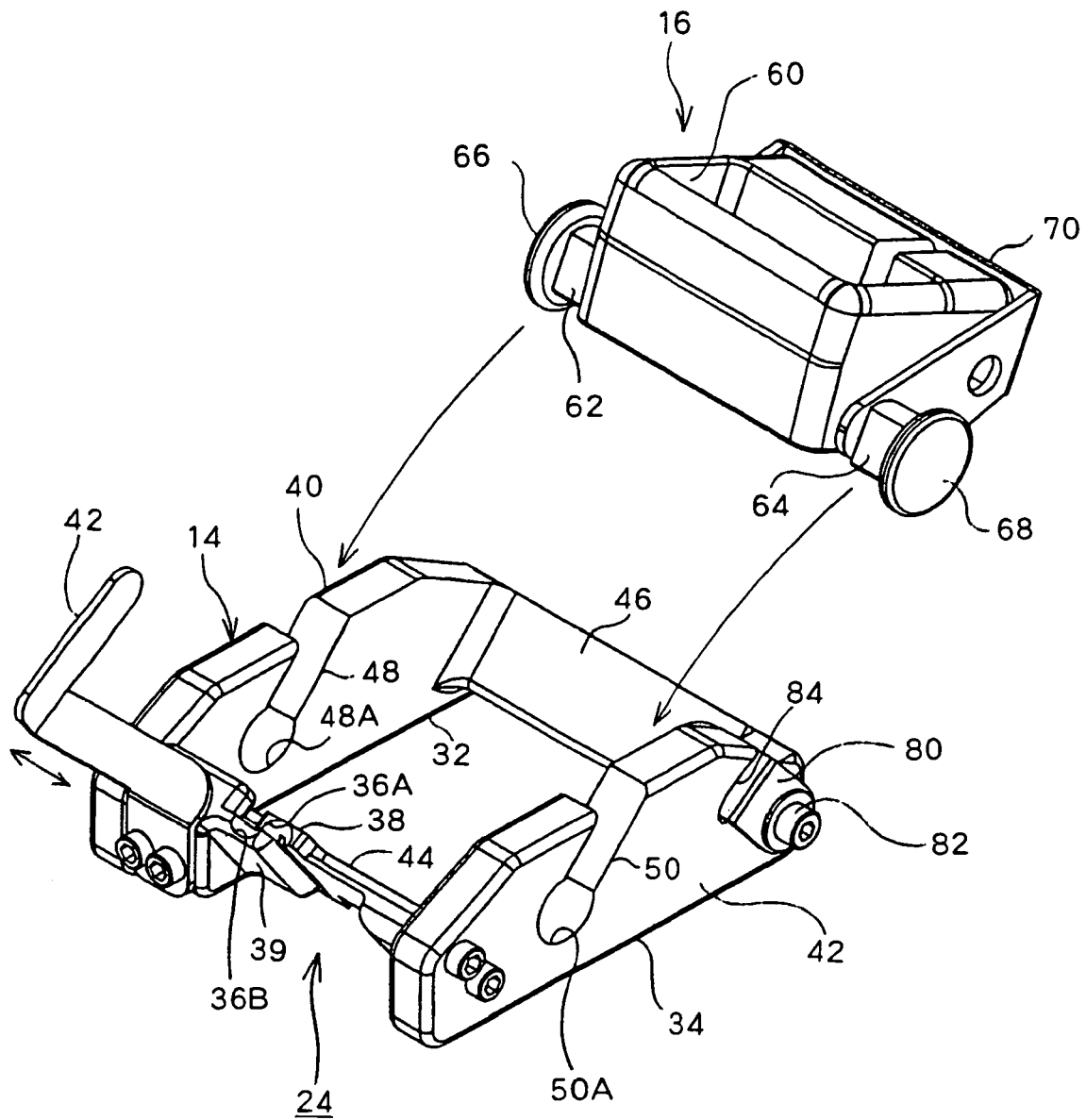
FIG. 4 is an exploded perspective view of the puncture adapter according to the embodiment of the present invention.

The puncture adapter 12 will be described in further detail. FIG. 4 shows a state in which the holder 16 is detached from the base unit 14. As such, the holder 16 and the base unit 14 can be separated from each other, as necessary for disinfection, cleaning, sterilization, and other processes.

The base unit 14 will be described first. The base unit 14 includes side plates 40 and 42 which are disposed towards the right and left directions at a fixed interval, and a front plate 44 and a back plate 46 are provided on the front and back portions between these side plates 40 and 42. Thus, these plates 40 to 46 form a rectangular frame. The side plates 40 and 42 have slots 48 and 50 formed therein and shaft holes 48A and 50A are formed at the bottom of the slots 48 and 50, respectively.

The piece 38 of the guide mechanism 24 which is described above is coupled to the front plate 44. FIG. 4 shows a state where the other piece 39 is retreated from the one piece 39, i.e. a state where the guide hole 36 is opened. A stopper 80 which is rotatably supported at the axis of rotation 82 is provided on the back side of the base unit 14. This stopper 80 is to be slid down into a slit 84 formed in the side plate 42, in which state the holder 16 is prevented from rotating further toward the back side. Specifically, a portion of the holder 16 strikes against the stopper 80 and further rotation of the holder 16 is restricted. Here, by removing the stopper 80 from the slit 84, further rotation of the holder 16 is allowed, and in this state, removal of the holder 16 from the base unit 14 and assemble of the holder 16 onto the base unit 14 can be achieved, as will be described below.

The holder 16 includes a housing portion 60 for receiving the probe 10. The housing portion 60 has an upper opening and a lower opening, and the wave transmitting and receiving surface of the probe 10 projects (is exposed) through the lower opening, as already described with reference to FIGS. 1 and 2. Shafts 62 and 64 are provided at right and left ends of the holder 16. The shafts 62 and 62 partially have a rectangular cross section as shown, and are inserted into the slots 48 and 50 at a fixed angle. When the shafts 62 and 64 reaches the furthest depth of the slots 48 and 50, respectively, the rotation of the shafts 62 and 64 is allowed by means of the shaft holes 48A and 50A as described above. Discs 66 and 68 are provided on the outer sides of the shafts 62 and 64, respectively. The holder 16 itself having the housing portion 60 is attached to a metal fitting 70, to which the shafts 62 and 64 as described above are fixed.

Figure 5:
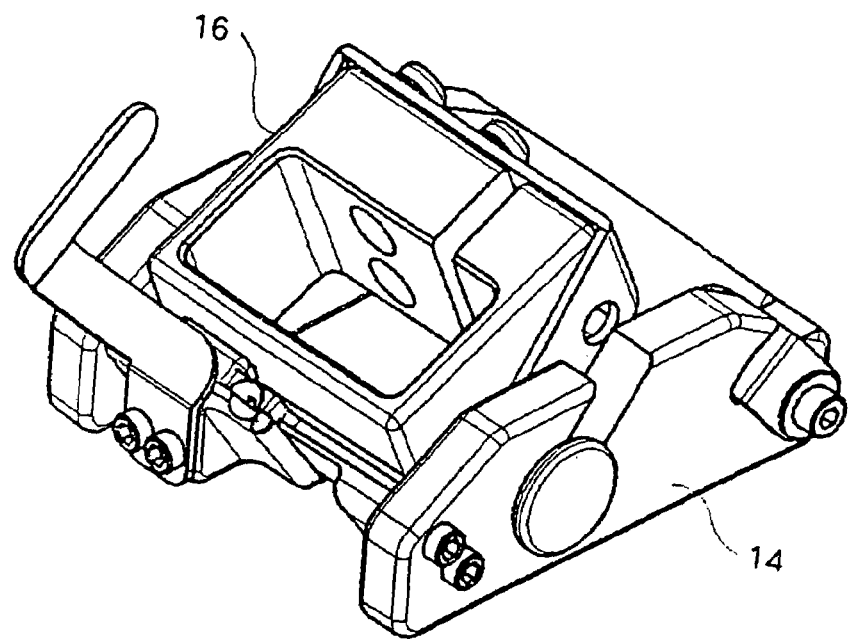
FIG. 5 is a perspective view of the puncture adapter according to the embodiment of the present invention, seen diagonally from the front.
Figure 6:
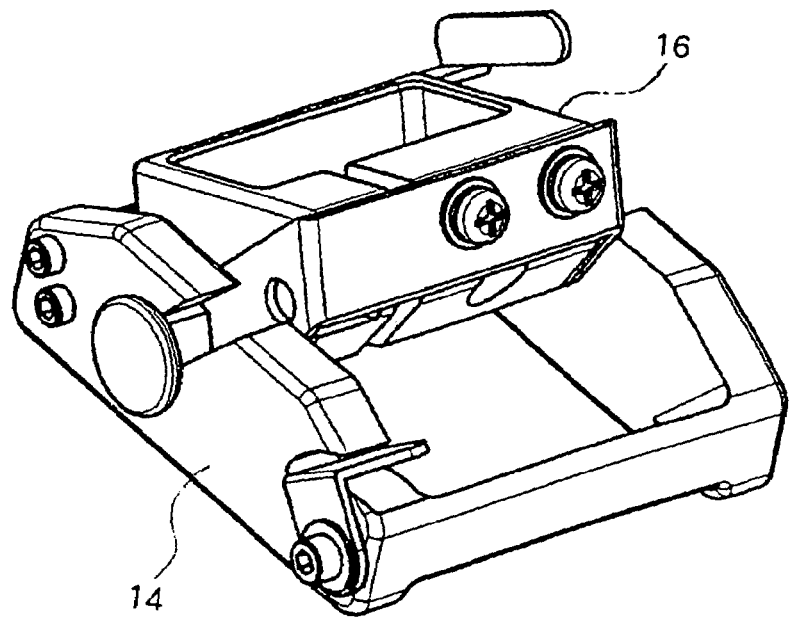
FIG. 6 is a perspective view of the puncture adapter according to the embodiment of the present invention, seen diagonally from the rear.
Figure 7:
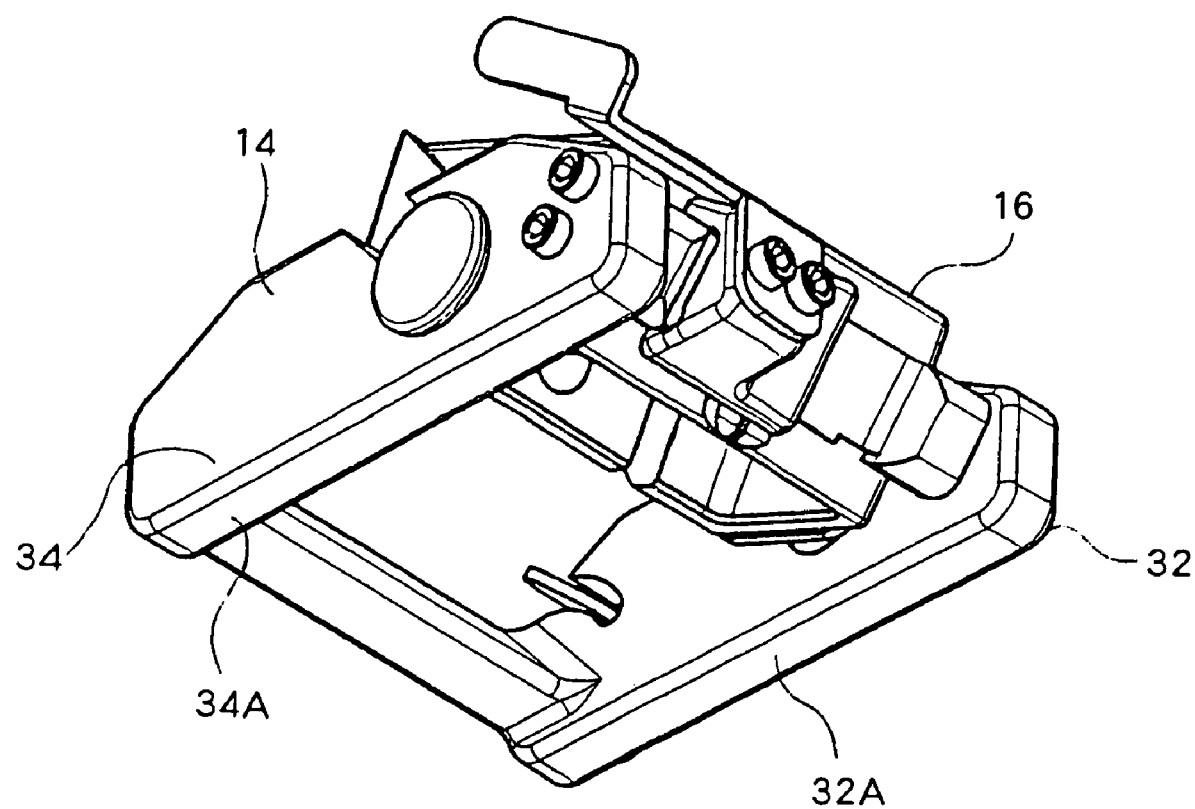
FIG. 7 is a perspective view of the puncture adapter according to the embodiment of the present invention, seen diagonally from beneath.

FIGS. 5 to 7 show perspective views of the puncture adapter. More specifically, FIG. 5 is a perspective view of the puncture adapter seen diagonally from the front side, FIG. 6 is a perspective view of the puncture adapter seen diagonally from the back side, and FIG. 7 is a perspective view of the puncture adapter seen diagonally from beneath. As shown in FIG. 7, a pair of leg portions 32 and 34 are provided on both sides of the moving region of the wave transmitting and receiving surface at an interval between them, and the lower surfaces of the leg portions 32 and 34 form contact surfaces 32A and 34A, respectively. By bringing these contact surfaces 32A and 34A in contact with the surface of a subject in such a manner that a pair of skis are placed, a problem that a pressing force is concentrated onto the blood vessel located under the moving space of the wave transmitting and receiving surface can be prevented.

Figure 8:
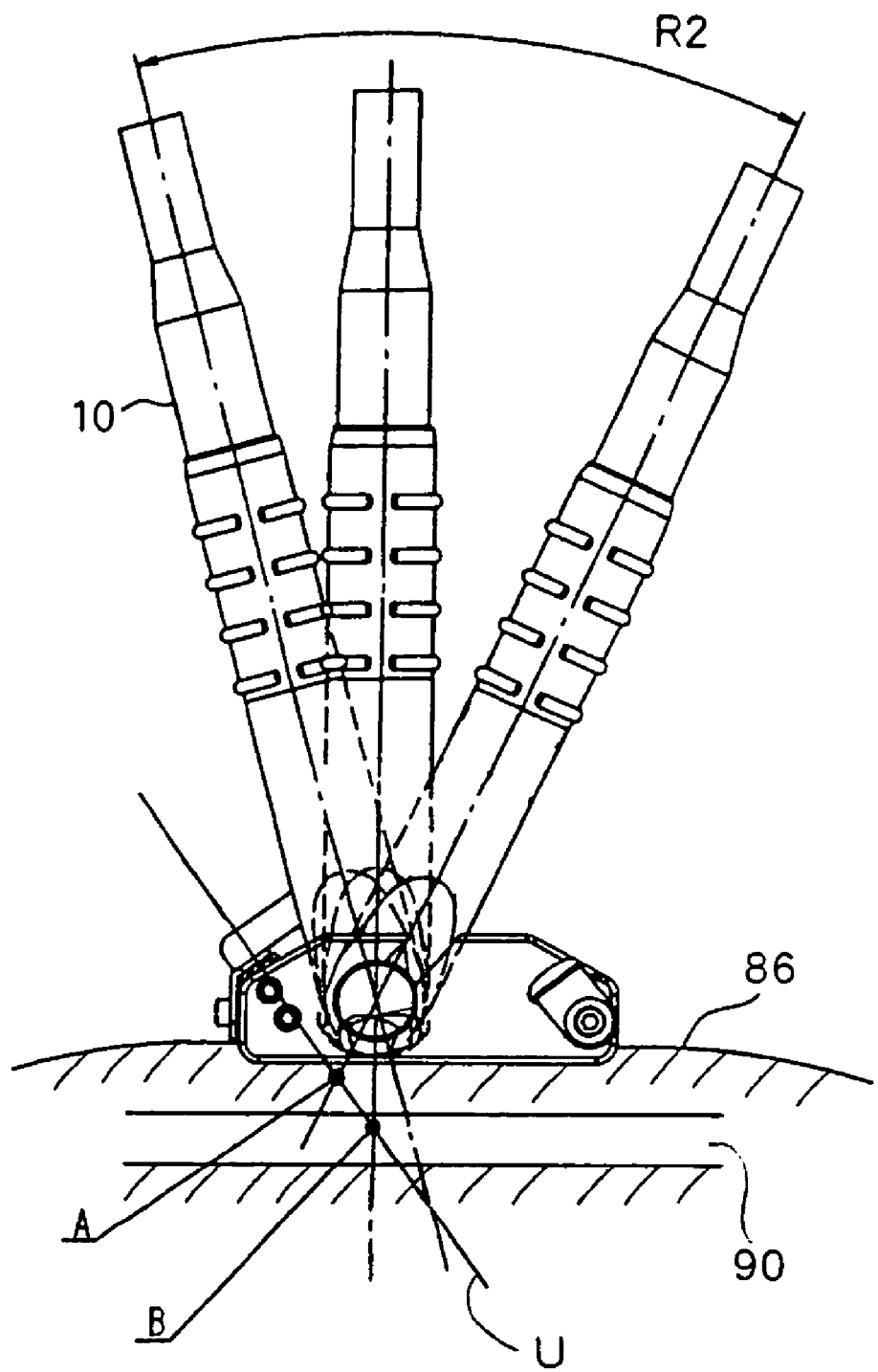
FIG. 8 is a view for explaining an operation of a probe following the puncture.
Figure 9A:
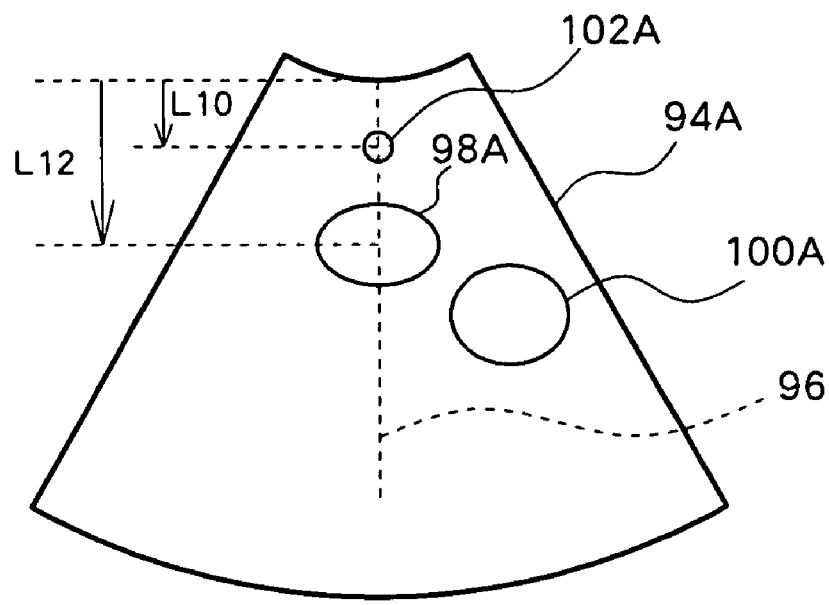
FIG. 9A is an explanatory view showing the content of an ultrasonic image in a state of a first insertion depth.
Figure 9B:
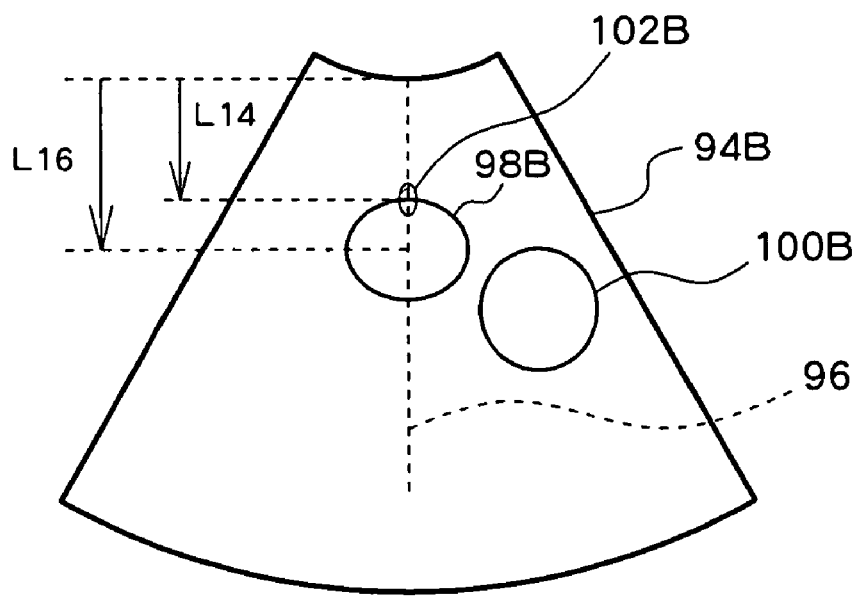
FIG. 9B is an explanatory view showing the content of an ultrasonic image in a state of a second insertion depth.

Referring to FIGS. 8, 9A and 9B, an example usage of the puncture adapter according to the present embodiment will be described. First, the probe is attached to the holder, and the holder which now holds the probe is assembled with the base unit. In this assembled state, the puncture adapter is brought into contact with the neck portion of a human body, for example, and this state is maintained. Alternatively, it is also possible to first set the holder before attaching the probe onto the holder. At this time, the direction and the position of the puncture adapter is manually adjusted such that the puncture route is appropriately set diagonally along the axial direction of the jugular vein, for example. When performing such an adjustment, an ultrasonic image may be observed. In a state where the puncture adapter is positioned, puncture is performed using the guide mechanism as described above. In the process of the puncture, the puncture needle is gradually inserted into the body. At this time, by appropriately changing the pivoting angle of the probe 10 as shown in FIG. 8, a cross section at various positions on the puncture route U can be observed on a tomographic image. In FIG. 8, numeral 86 denotes a surface of the living body, and numeral 90 denotes a jugular vein which is a subject of the puncture. The carotid artery near the jugular vein is not shown in FIG. 8.

As described above, by causing the probe 10 to pivot, and more specifically, by locating the position of the tip of the puncture needle by a big pivoting motion and further causing the probe 10 to slowly reciprocate in the vicinity of the located position, the position of the tip of the puncture needle can be reliably recognized. Thus, the positional relationship between the tip of the puncture needle and each organ within the living body can be grasped easily. Specifically, it is possible to confirm that the jugular vein is appropriately punctured and that the puncture direction is not erroneously set toward a wrong blood vessel.

FIGS. 9A and 9B show tomographic images corresponding to the scan planes passing through points A and B, respectively, in FIG. 8. Specifically, FIG. 9A shows a tomographic image corresponding to the point A, and FIG. 9B shows a tomographic image corresponding to the point B. As will be understood from the positional relationship shown in FIG. 8, the structure which is observed on the tomograhpic image changes slightly in accordance with the movement of the scan plane.

Referring to FIG. 9A, the cross section 98A of the jugular vein and the cross section 100A of the carotid artery are shown on the tomographic image 94A. In this case, the tomographic image shows a marker indicated by numeral 96, which corresponds to the puncture route. Numeral 102A represents an image corresponding to the tip of the puncture needle. At this stage, the tip of the puncture needle reaches the depth indicated by L10 and the distance from the wave transmitting and receiving surface to the center of the jugular vein corresponds to L12.

FIG. 9B shows a tomographic image 94B corresponding to the point B, in which the cross section 98B of the jugular vein and the cross section 100B of the carotid artery are similarly shown. In this case, the depth to the center of the jugular vein corresponds to L16. The tomographic image 94B also shows an image 102B corresponding to the tip of the puncture needle which reaches the depth L14, where the tip of the puncture needle reaches the jugular vein.

Accordingly, when the scan plane is fixed with respect to the puncture route such that the scan plane intersects the puncture route, an image of the tip of the puncture needle cannot be obtained until the tip of the puncture needle reaches the scan plane. According to the present embodiment, on the contrary, the scan plane can be moved in each process of the puncture for detecting the tip of the puncture needle and the positional relationship between the puncture route and each organ can also be grasped easily on a tormographic image. Consequently, information similar to that obtained by performing three-dimensional ultrasonic diagnosis can be obtained, advantageously enhances the safety of the puncture procedure, with but a simple structure.

Here, a plurality of types of holders and base units may be prepared corresponding to types of probe or the like. Further, while the puncture angle of the puncture needle is fixed in the above embodiment, a mechanism which allows the puncture angle to be variable may be provided. Further, while in the above embodiment, dispersion of a pressing force is achieved by a pair of leg portions such that a blood vessel which is a subject of puncture will not be collapsed, other structures corresponding to the pair of leg portions may be adopted. For example, a contact surface having a rectangular frame shape or a contact surface having a shape in which one of four sides of a rectangle is removed may be used. In addition, the movement of the probe is not limited to a pivoting movement described above, and may be a translation movement or a rotation movement. After puncture is performed, a predetermined treatment including insertion of a catheter and injection of medicine is performed.

Figure 10:
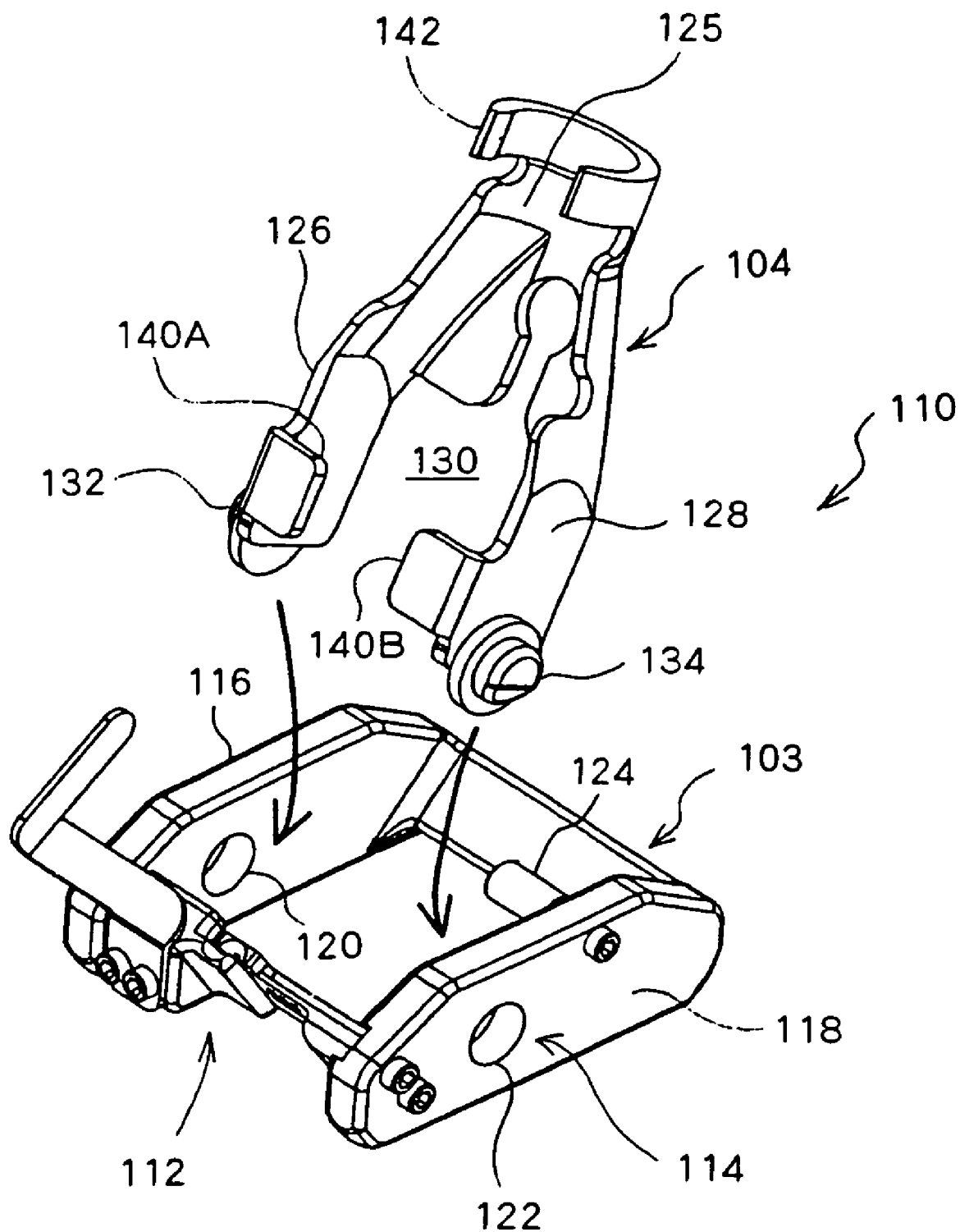
FIG. 10 is a perspective view of an adapter for use in puncture according to another embodiment of the present invention.
Figure 11:
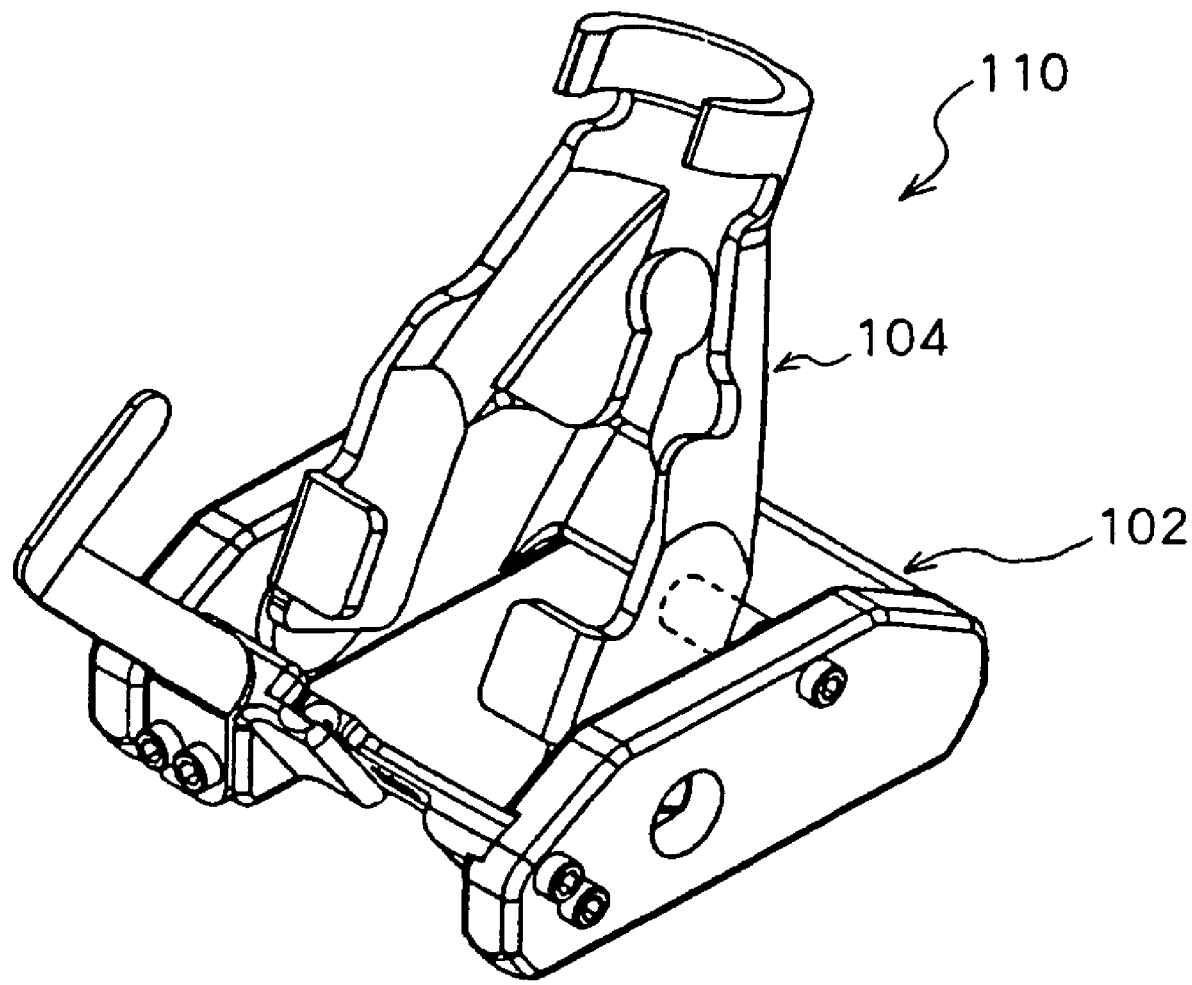
FIG. 11 is a perspective view showing a state in which the holder is mounted onto the base unit.

In FIGS. 10 and 11, a puncture adapter 110 according to another embodiment of the present invention is shown. Similar to the embodiment described above with reference to FIGS. 1 and 2 and other drawings, the puncture adapter 110 includes a base unit 103 and a holder 104. The base unit 103 includes a guide mechanism 112 and a moving mechanism 114. The guide mechanism 112 has a structure similar to that of the above-described embodiment.

As shown, two side plates 116 and 118 of the base unit 103 have shaft holes 120 and 122 formed therein, respectively. Here, numeral 124 denotes a stopper which restricts the movement of the holder 104 in one direction as will be described below.

The upper portion 125 of the holder 104 bifurcates downward to form two arms 126 and 128, which, in a normal state, are spaced apart from each other with a fixed interval therebetween. Each of the arms 126 and 128 is elastically deformable, and therefore the distance between them can be reduced. Each of the arms 126 and 128 has a disc shape outward projection 132 or 134 at the lower end thereof. A cavity within the holder 104 provides as a housing space for the probe.

Prior to mounting of the probe onto the holder 104, the two arms 126 and 128 of the holder 104 are deformed to bring them closer to each other, and, in this state, the projections 132 and 134 are inserted into the shaft holes 120 and 122 of the base unit 103, respectively, as shown in FIG. 11. Here, in such a state where the holder 104 is attached onto the base unit 103, the holder 104 is allowed to pivot about the axis of rotation similar to the above-described embodiment. Here, falling of the holder 104 down towards the front side is restricted by contact of the holder 104 onto the front plate, and falling of the holder 104 down towards the back side is restricted by the stopper 124 shown in FIG. 10.

After the holder 104 is set onto the base unit 103, the probe is set onto the holder 104. As shown in FIGS. 10 and 11, the interior space 130 of the holder 104 is configured so as to allow the probe to be mounted onto the holder through the front side of the holder 104. More specifically, the lower portion of the probe is first inserted into the interior (inside the hooks 140A and 140B) of the holder 104, and the upper portion of the probe is then inserted into a clip 142 formed on the top portion of the holder 104, whereby the probe can be reliably held by the holder 104.

According to the embodiment shown in FIGS. 10 and 11, the holder 104 can be easily set onto the base unit 103 using the elastic effect of the two arms 126 and 128. It is of course possible to adopt other structures as long as a mechanism which allows the probe to move relative to the puncture route is adopted.

Figure 12:
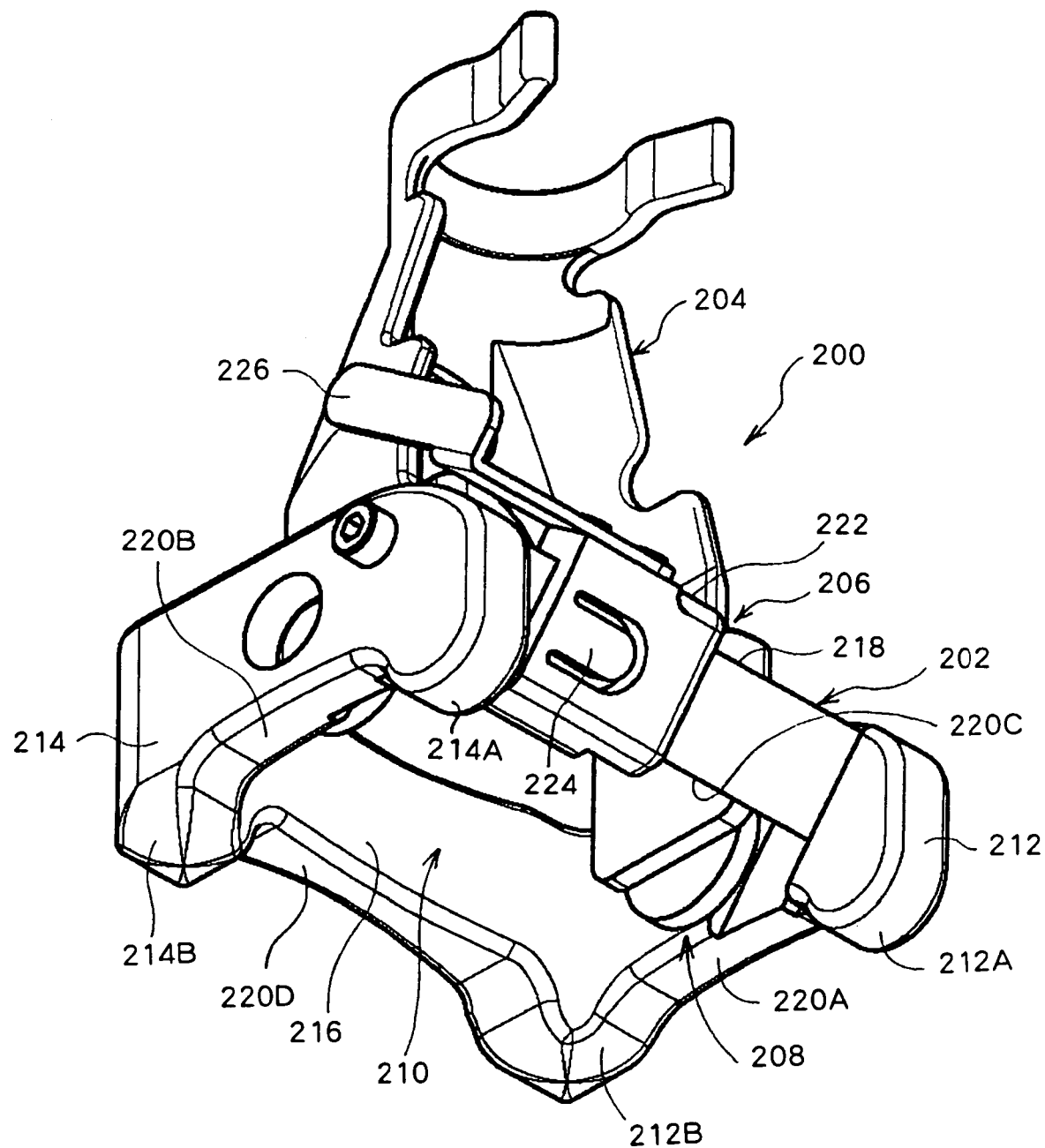
FIG. 12 is an adapter for use in puncture according to still another embodiment of the present invention.

Referring to FIGS. 12 to 16, a puncture adapter according to a further embodiment will be described. FIG. 12 is a perspective view of a puncture adapter 200.

Figure 13:
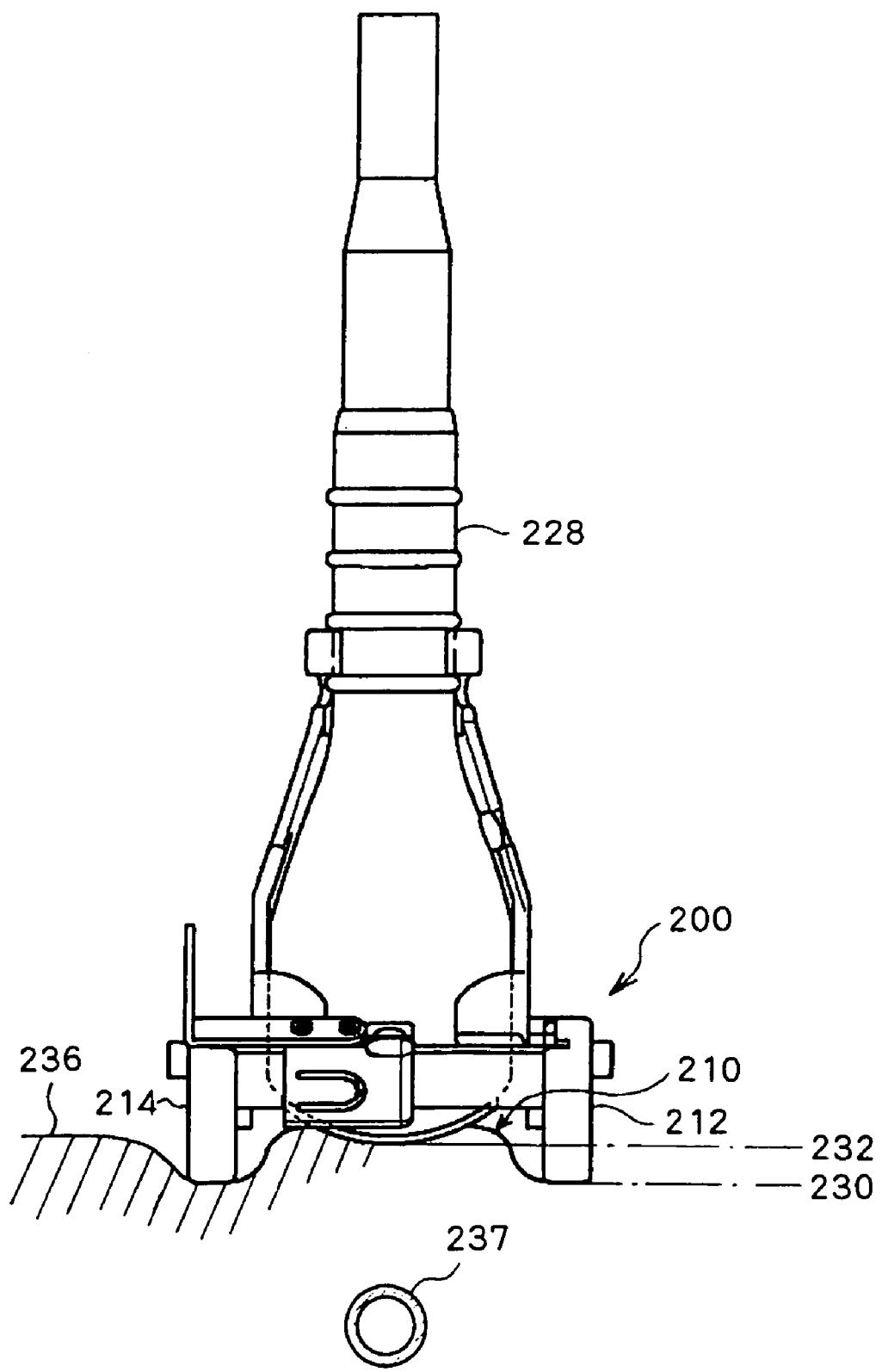
FIG. 13 is a front view of the puncture adapter shown in FIG. 12.

Referring to FIG. 12, the puncture adapter 200 includes a base unit 202 and a holder 204. The holder 204 detachably holds a probe which is shown in FIG. 13 or the like. The base unit 202 functions as a seat and is brought into contact with a surface of a living body. The base unit 202 includes a moving mechanism 208 and a guide mechanism 206. The moving mechanism 208 causes the holder 204 to rotate with respect to the base unit 202. The guide mechanism 206 guides a puncture needle which is not shown.

The base unit 202 includes a pair of leg portions (a pair of side plates) 212 and 214 spaced apart from each other with a rectangular movement region 210 in which the wave transmitting and receiving surface of the probe moves being interposed therebetween. The base unit 202 also includes a fixed piece 218 serving as a front plate and a back plate 216, which are provided between the pair of leg portions 212 and 214. The leg portion 212 includes a pair of projecting legs 212A and 212B on both ends. Similarly, the leg portion 214 includes a pair of projecting legs 214A and 214B on both ends. In other words, the four projecting legs 212A, 212B, 214A, and 214B are provided along the periphery of the rectangular movement region 210 corresponding to four corners thereof, respectively. Each projecting leg 212A, 212B, 214A, or 214B projects toward the living body side and has a contact surface as a tip end surface which is rounded so as not to cause pain or discomfort. The projecting leg has a semicylindrical or hemispherical shape. The number of projecting legs can be set arbitrarily as long as a target tissue is not deformed more than desirable, with four legs generally being preferable.

In the leg portion 212, an arch shape recess 220A is formed between the pair of projecting legs 212A and 212B. Similarly, in the leg portion 214, an arch shape recess 220B is formed between the pair of projecting legs 214A and 214B. Further, in the back plate 216, an arch shape recess 220D is formed between a pair of projecting legs 212B and 214B. In addition, with regard to the fixed piece 218 serving as the front plate, an arch shape recess 220C is also recognized between a pair of projecting legs 212A and 214A.

The guide mechanism 206 includes the fixed piece 218, a sliding piece 222, a lever 226, and so on. Here, the sliding piece 222 includes an elastic small piece 224 which is integrally formed with the sliding piece 222, as will be described in detail with reference to FIG. 15. According to the present embodiment, the fixed piece 218 is made of a metal, and the sliding piece 222 is made of a resin for convenience of machining.

Figure 14:
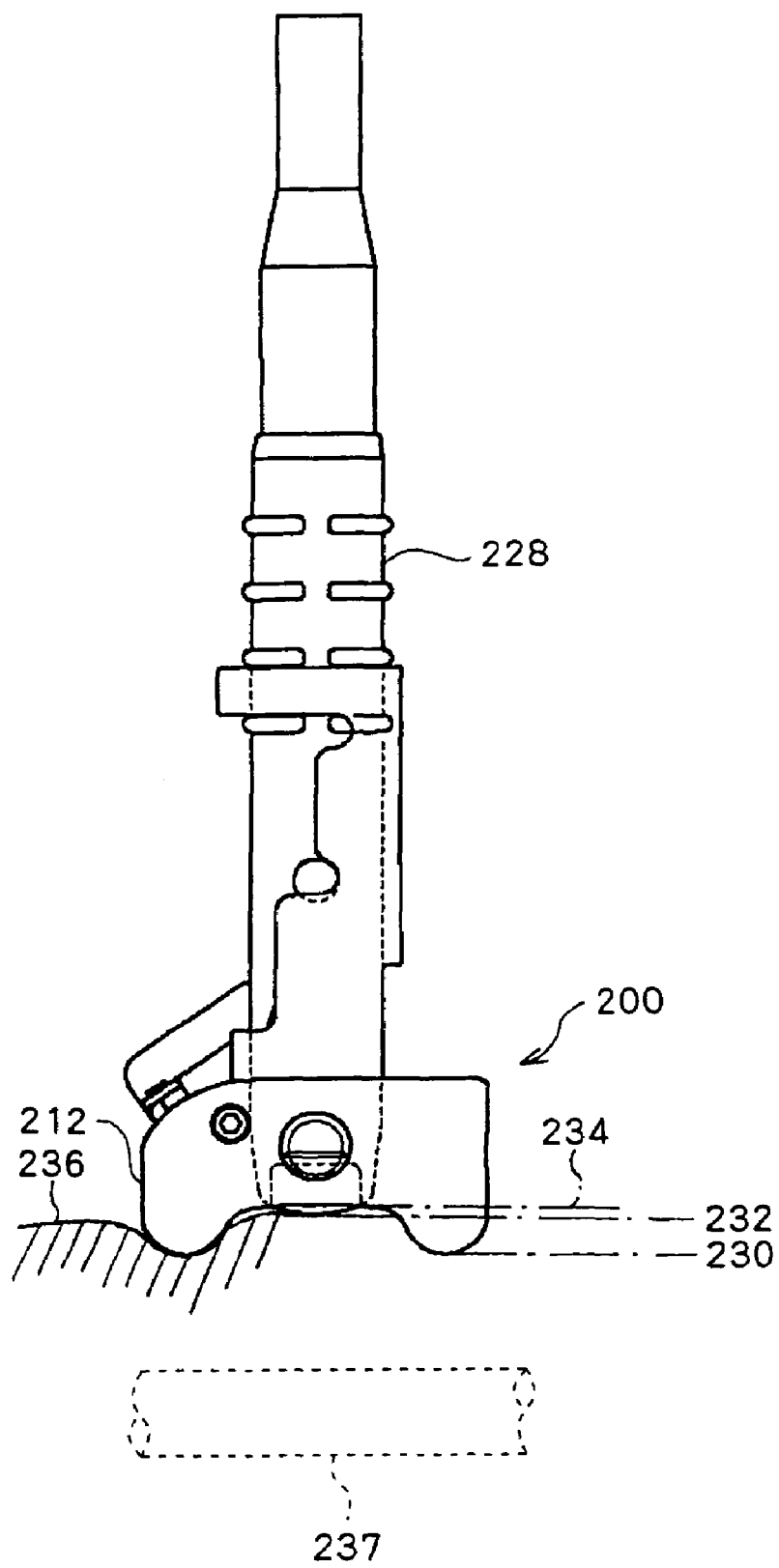
FIG. 14 is a side view of the puncture adapter shown in FIG. 12.

FIGS. 13 and 14 show a state in which the probe 228 is mounted onto the puncture adapter 200 shown in FIG. 12.

FIG. 13 shows a front view and FIG. 14 shows a side view. The level 232 of the wave transmitting and receiving surface of the probe is set higher (by 8 mm, for example) than the level 230 of the tip end surface of each projecting leg in the leg portions 212 and 214. Further, the level 234 of the ceiling surface of the arch shape recess is set at a position slightly higher than the level 232.

In the process of bringing the puncture adapter 200 in contact with the living body surface 236, the tip end surface (contact surface) of each projecting leg depresses the living body surface 236. At the same time, the living body surface 236, in a relatively lifted state, comes into the movement region 210 of the wave transmitting and receiving surface and each arch shape recess. This brings the wave transmitting and receiving surface of the probe 228 in close contact with the living body surface 236. In this case, preferable close contact can be maintained even when the probe 228 rotates. In FIGS. 13 and 14, numeral 237 denotes a blood vessel (a jugular vein, for example) running within a body. The puncture adapter 200 is positioned on the body surface 236 such that the scan plane intersects the axial direction of such a blood vessel 237. More specifically, the pair of leg portions 212 and 214 are positioned across the blood vessel 237 (FIG. 13). The pressing force generated at the time of contacting is dispersed mainly into the four projecting legs and is then applied to the living body surface 236 where the stress (the pressing force) is concentrated. Thus, because a large pressing force is not applied to the movement region 210 (especially the region immediately below the wave transmitting and receiving surface), it is possible to reduce or solve the problem of deformation or collapse of the blood vessel while close contact between the wave transmitting and receiving surface and the living body surface 236 is secured. In FIG. 14, the blood vessel 237 is located immediately below the intermediate position between two leg portions, and not immediately below any one leg portion. While deformation or collapse of blood vessel can be reduced to a certain degree by the embodiment shown in FIG. 1, the present embodiment can more effectively cope with this problem.

Figure 15:
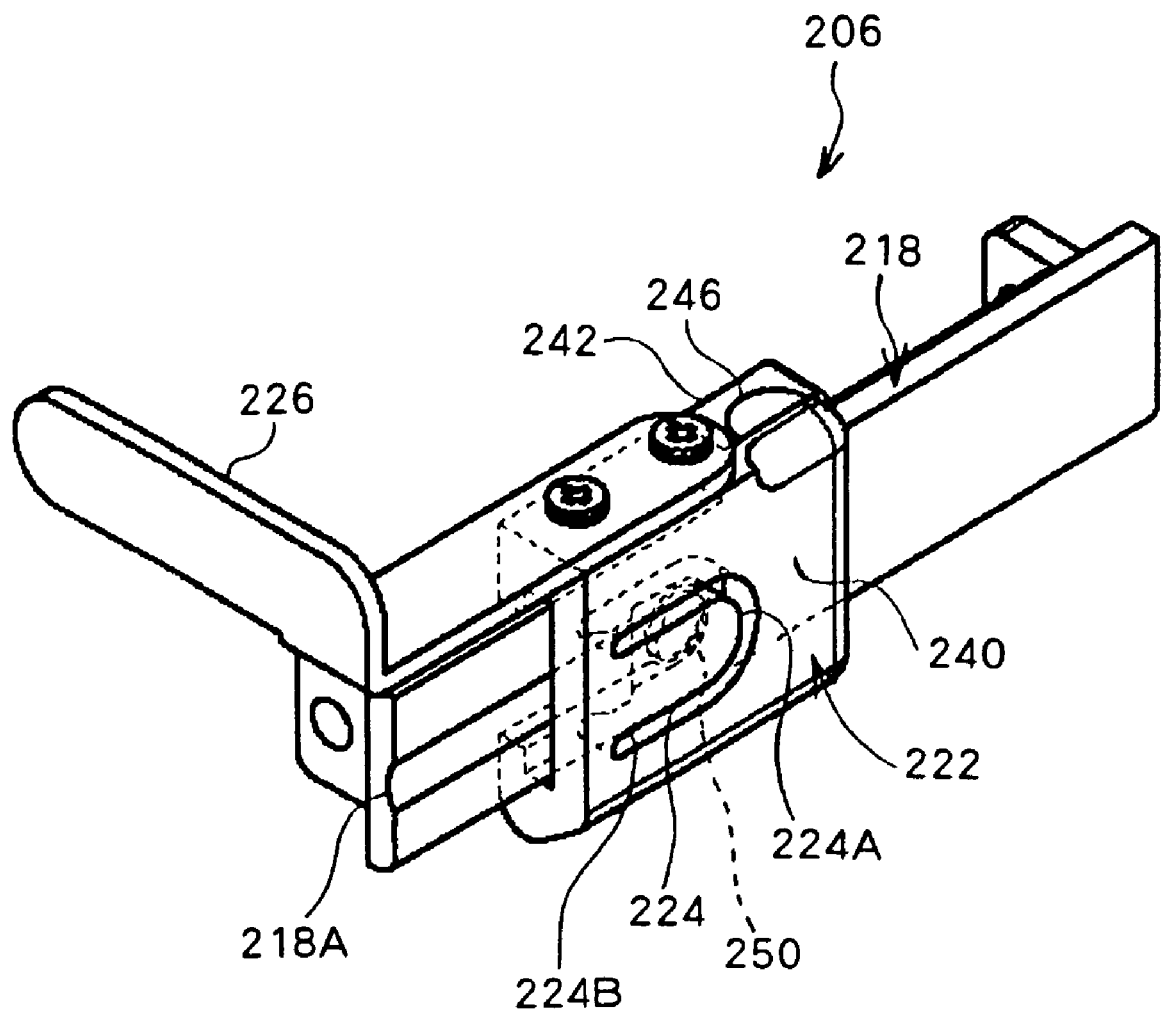
FIG. 15 is an enlarged view of the guide mechanism.

FIG. 15 is an enlarged view of the guide mechanism 206. The guide mechanism 206 includes the fixed piece 218 and the sliding piece 222. The fixed piece 218 includes a slide slot 218A formed therein. A hemispherical recess which is deeper than the slot 218A is formed on one end of the slide slot 218A. The sliding piece 222 includes one side portion 240 and the other side portion 242, and the elastic small piece 224 is provided on the one side portion 240. A hemispherical projection 250 projecting toward the fixed piece 218 is formed on one end portion 224A of the elastic small piece 224, and the projection 250 is continuously pressed against the fixed piece 218 by means of the elastic effect of the elastic small piece 224. The other end 224B of the elastic small piece 224 is integrally formed with the sliding piece 222. Numeral 246 denotes an opening edge through which a puncture needle is inserted. The lever 226 is coupled with the sliding piece 222 and can be operated for causing the sliding piece to advance and retreat.

Figure 16:
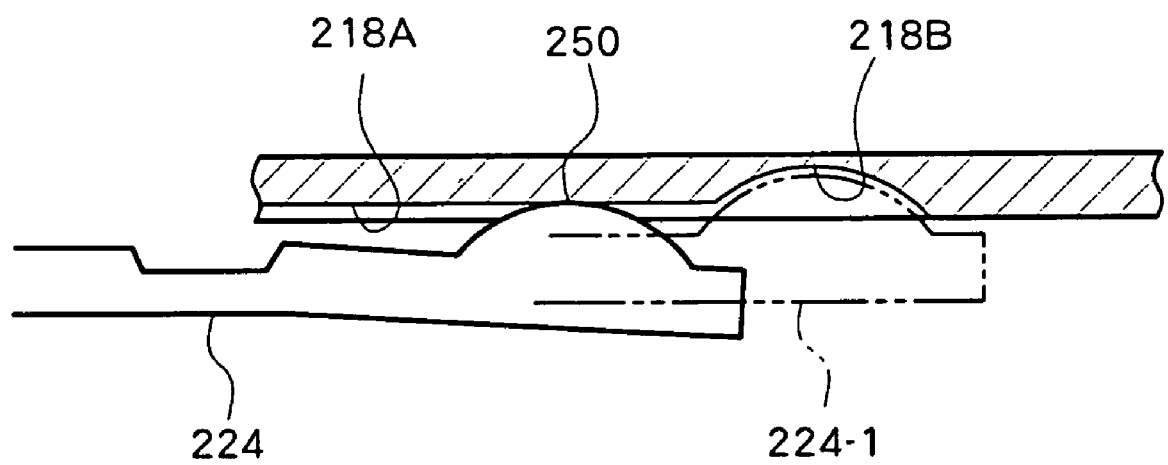
FIG. 16 is a view for explaining an effect of the guide mechanism.

In FIG. 16, an operation of the sliding piece 222 is shown. In a state wherein the sliding piece is moved to the forward end, as indicated by numeral 224-1, the projection 250 fits down into the recess 218B (i.e. the projection 250 is trapped in the recess 218B), whereby the position of the sliding piece is held. The puncture needle is inserted into the guide hole in this state. Then, when the user causes the sliding piece to retreat, the projection 250 is withdrawn from the recess 218B and slides along the slot 218A. In this state in which the guide hole is opened (i.e. the guide slot is exposed), the puncture adapter, along with the probe, can be shifted laterally (to the back side) to be detached from the puncture needle, which remains in the puncturing state. With the guide mechanism described above, it is possible to prevent inadvertent movement of the sliding piece by engagement between the projection 250 and the recess 218B, so that erroneous release of the puncture needle during a puncture procedure can be prevented. Thus, safety of the device can be enhanced. In the above structure, while various shapes may be adopted as the shape of the tip of each projecting leg, the projecting tip which is rounded is desirable so as not to cause pain or discomfort.

While the preferred embodiments of the present invention have been described using specific terms, such description is for illustrative purposes only, and it is to be understood that changes and variations may be made without departing from the spirit or scope of the appended claims.

What is claimed is:

1. An adapter for use in puncture to be attached to a probe which transmits and receives an ultrasonic wave, the adapter comprising:
    a holder for holding the probe;
    a base unit including a guide mechanism for guiding a puncture needle, a seat for contacting a surface of a subject and a moving mechanism for movably supporting the holder such that when a probe is held in the holder, the holder moves a wave transmitting and receiving region of the probe relative to a puncture route of the puncture needle such that a beam scan plane intersects the puncture route and an intersection between the puncture route and the beam scan plane moves along the puncture route; and whereby
    the puncture route diagonally penetrates a beam scan plane from the front side to the back side, and when the beam scan plane moves with a move of the holder by the moving mechanism, an intersection between the puncture route and the beam scan plane moves along the puncture route; and wherein
    the seat has a pair of leg portions provided with a movement region of the wave transmitting and receiving surface of the probe interposed therebetween; and
    the base unit allows the holder to move such that the wave transmitting and receiving surface of the probe is continuously in close contact with the surface of the subject.

2. An adapter for use in puncture according to claim 1, wherein
    the moving mechanism causes the holder to pivot about a rotation center axis which is spaced apart from the puncture route.

3. An adapter for use in puncture according to claim 2, wherein
    the moving mechanism restricts pivoting movement of the holder such that the intersection moves in a range from a first observation position at a shallower depth on the puncture route to a second observation position at a deeper depth on the puncture route.

4. An adapter for use in puncture according to claim 1, wherein
    the holder is a member which detachably holds the probe while directing a wave transmitting and receiving surface of the probe toward a subject, and the holder is removably assembled onto the base unit.

5. An adapter for use in puncture according to claim 1, wherein
    the guide mechanism is a mechanism for holding and releasing the puncture needle and guides the puncture needle in a direction which is inclined with respect to the base unit.

6. An adapter for use in puncture according to claim 5, wherein
    the guide mechanism includes a lever which opens and closes a guide hole through which the puncture needle is inserted, and the guide hole is opened and closed by a sliding operation of the lever.

7. An adapter for use in puncture according to claim 1, wherein
the guide mechanism includes a fixed piece and a sliding piece which performs sliding movement with respect to the fixed piece for holding and releasing the puncture needle,
a recess is formed on one of the fixed piece and the sliding piece, and
a projection which is fitted down into the recess when the sliding piece advances and which is withdrawn from the recess when the sliding piece retreats is formed on the other one of the fixed piece and the sliding piece.

8. An adapter far use in puncture according to claim 1, wherein
each of the leg portions has a flat contact surface extending in parallel to each other in the moving direction of the wave transmitting and receiving surface.

9. An adapter for use in puncture to be attached to a probe which transmits and receives an ultrasonic wave for performing puncture with respect to a target blood vessel under observation on a tomographic image, the adapter comprising:
a holder for holding the probe; and
a base unit to be disposed on a surface of a subject, the base unit movably supporting the holder,
wherein
the base unit includes:
a seat which is brought in contact with the surface of the subject;
a guide mechanism for guiding a puncture needle with respect to the target blood vessel in a diagonal direction along the axial direction of the target blood vessel;
a moving mechanism for movably supporting the holder which holds the probe, such that a beam scan plane generated by the probe intersects a puncture route of the puncture needle and the target blood vessel in each movement position such that a beam scan plane intersects the puncture route and an intersection between the puncture route and the beam scan plane moves along the puncture route; and whereby
the puncture route diagonally penetrates a beam scan plane from the front side to the back side, and when the beam scan plane moves with a move of the holder by the moving mechanism, an intersection between the puncture route and the beam scan plane moves along the puncture route; and wherein
the seat has a pair of leg portions provided with a movement region of the wave transmitting and receiving surface of the probe interposed therebetween; and
the base unit allows the holder to move such that the wave transmitting and receiving surface of the probe is continuously in close contact with the surface of the subject.

10. An adapter for use in puncture according to claim 9, wherein
the moving mechanism is a mechanism which causes the holder to perform pivoting movement;
the puncture route is fixed independent of the pivoting movement of the holder, and
an intersection between the beam scan plane and the puncture route moves along a center line of the beam scan plane within a predetermined depth range.

11. An adapter for use in puncture according to claim 9, wherein
the seat is brought in contact with a neck portion of the subject, and
the target blood vessel is a jugular vein.

12. An adapter for use in puncture to be attached to a probe which transmits and receives an ultrasonic wave, the adapter comprising:
a holder for holding the probe; and
a base unit including a guide mechanism for guiding a puncture needle, a seat for contacting a surface of an object and a moving mechanism for movably supporting the holder to move a wave transmitting and receiving region of the probe relative to a puncture route of the puncture needle,
wherein:
the seat includes a plurality of rounded projecting leg portions, the plurality of projecting leg portions being provided with a movement region of a wave transmitting and receiving surface of the probe interposed therebetween and being brought in contact with a surface of a subject such that a beam scan plane which is the wave transmitting and receiving region intersects the puncture route and an intersection between the puncture route and the beam scan plane moves along the puncture route; and whereby
the puncture route diagonally penetrates a beam scan plane from the front side to the back side, and when the beam scan plane moves with a move of the holder by the moving mechanism, an intersection between the puncture route and the beam scan plane moves along the puncture route; and wherein
the base unit allows the holder to move such that the wave transmitting and receiving surface of the probe is continuously in close contact with the surface of the subject.

13. An adapter for use in puncture according to claim 12, wherein
the plurality of projecting leg portions are provided at four positions corresponding to four corners of the movement region.

14. An adapter for use in puncture according to claim 12, wherein
the plurality of projecting leg portions include a first projecting leg and a second projecting leg provided on one side of the movement region and a third projecting leg and a fourth projecting leg provided on the other side of the movement region,
a first arch portion is formed between the first projecting leg and the second projecting leg,
a second arch portion is formed between the third projecting leg and the fourth projecting leg,
a third arch portion is formed between the first projecting leg and the third projecting leg, and
a fourth arch portion is formed between the second projecting leg and the fourth projecting leg.

15. An adapter for use in puncture according to claim 12, wherein
in a state wherein the base unit is pressed onto the surface of the subject, a pressing force is conveyed from the plurality of projecting leg portions to the subject, such that a portion of the surface of the subject within the movement region is lifted upwards, and
in the state wherein the portion of the surface of the subject is lifted upwards, the wave transmitting and receiving surface of the probe comes in contact with the portion of the surface of the subject independent of a moving position of the probe.

* * * * *